United States Patent [19]

Lapidus et al.

[11] Patent Number: 5,741,650
[45] Date of Patent: *Apr. 21, 1998

[54] METHODS FOR DETECTING COLON CANCER FROM STOOL SAMPLES

[75] Inventors: Stanley N. Lapidus, Bedford, N.H.; Anthony P. Shuber, Milford; Kevin M. Ulmer, Cohasset, both of Mass.

[73] Assignee: Exact Laboratories, Inc., Maynard, Mass.

[21] Appl. No.: 699,678

[22] Filed: Aug. 14, 1996

Related U.S. Application Data

[60] Provisional application No. 60/010,856 Jan. 30, 1996.

[51] Int. Cl.⁶ .................................................. C12Q 1/68
[52] U.S. Cl. ...................................................... 435/6
[58] Field of Search ........................................ 435/6, 7.1

[56] References Cited

U.S. PATENT DOCUMENTS

| | | | |
|---|---|---|---|
| 4,101,279 | 7/1978 | Aslam | 23/259 |
| 4,309,782 | 1/1982 | Paulin | 4/661 |
| 4,333,734 | 6/1982 | Fleisher | 23/230 |
| 4,445,235 | 5/1984 | Slover et al. | 4/144.2 |
| 4,535,058 | 8/1985 | Weinberg et al. | 435/6 |
| 4,683,195 | 7/1987 | Mullis et al. | 435/6 |
| 4,705,050 | 11/1987 | Markham | 128/749 |
| 4,735,905 | 4/1988 | Parker | 436/174 |
| 4,786,718 | 11/1988 | Weinberg et al. | 435/6 |
| 4,857,300 | 8/1989 | Maksem | 424/3 |
| 4,871,838 | 10/1989 | Bos et al. | 536/27 |
| 4,981,783 | 1/1991 | Augenlicht | 435/6 |
| 4,982,615 | 1/1991 | Sultan et al. | 73/864.51 |
| 5,087,617 | 2/1992 | Smith | 514/44 |
| 5,126,239 | 6/1992 | Livak et al. | 435/6 |
| 5,137,806 | 8/1992 | LeMaistre et al. | 435/6 |
| 5,149,506 | 9/1992 | Skiba et al. | 422/102 |
| 5,196,167 | 3/1993 | Guadagno et al. | 422/56 |
| 5,248,671 | 9/1993 | Smith | 514/44 |
| 5,272,057 | 12/1993 | Smulson et al. | 435/6 |
| 5,330,892 | 7/1994 | Vogelstein et al. | 435/6 |
| 5,331,973 | 7/1994 | Fiedler et al. | 128/760 |
| 5,348,855 | 9/1994 | Dattagupta et al. | 435/6 |
| 5,352,775 | 10/1994 | Albertsen et al. | 536/23.1 |
| 5,362,623 | 11/1994 | Vogelstein et al. | 435/6 |
| 5,369,004 | 11/1994 | Polymeropoulos et al. | 435/6 |
| 5,379,602 | 1/1995 | Polymeropoulos et al. | 435/6 |
| 5,380,645 | 1/1995 | Vogelstein | 435/6 |
| 5,380,647 | 1/1995 | Bahar | 435/7.23 |
| 5,382,510 | 1/1995 | Levine et al. | 435/6 |
| 5,409,586 | 4/1995 | Kamahori et al. | 204/182.8 |
| 5,458,761 | 10/1995 | Kamahori et al. | 204/299 |
| 5,463,782 | 11/1995 | Carlson et al. | 4/661 |
| 5,466,576 | 11/1995 | Schulz et al. | 435/6 |
| 5,468,610 | 11/1995 | Polymeropoulos et al. | 435/6 |
| 5,468,613 | 11/1995 | Erlich et al. | 435/6 |
| 5,489,508 | 2/1996 | West et al. | 435/6 |
| 5,492,808 | 2/1996 | de la Chapelle et al. | 435/6 |
| 5,496,470 | 3/1996 | Lenhart | 210/222 |
| 5,508,164 | 4/1996 | Kausch et al. | 435/6 |
| 5,512,441 | 4/1996 | Ronal | 435/6 |
| 5,514,547 | 5/1996 | Balazs et al. | 435/6 |
| 5,527,676 | 6/1996 | Vogelstein et al. | 435/6 |
| 5,532,108 | 7/1996 | Vogelstein | 435/240.2 |

FOREIGN PATENT DOCUMENTS

| | | |
|---|---|---|
| A-11325/95 | 10/1994 | Australia. |
| 0 284 362 A2 | 9/1988 | European Pat. Off. |
| 0 337 498 | 10/1989 | European Pat. Off. |
| 0 390 323 A2 | 10/1990 | European Pat. Off. |
| 0 390 323 A3 | 10/1990 | European Pat. Off. |
| 0 407 789 A1 | 1/1991 | European Pat. Off. |
| 0 407 789 B1 | 1/1991 | European Pat. Off. |
| 0 608 004 A2 | 7/1994 | European Pat. Off. |
| 0 259 031 B1 | 11/1994 | European Pat. Off. |
| WO 92/13103 | 8/1992 | WIPO. |
| WO 93/20233 | 10/1993 | WIPO. |
| WO 94/00603 | 1/1994 | WIPO. |
| WO 94/10575 | 5/1994 | WIPO. |
| WO 95/07361 | 3/1995 | WIPO. |
| WO 95/09928 | 4/1995 | WIPO. |
| WO 95/12606 | 5/1995 | WIPO. |
| WO 95/13397 | 5/1995 | WIPO. |
| WO 95/15400 | 6/1995 | WIPO. |
| WO 95/16792 | 6/1995 | WIPO. |
| WO 95/18818 | 7/1995 | WIPO. |
| WO 95/19448 | 7/1995 | WIPO. |
| WO 95/25813 | 9/1995 | WIPO. |
| WO 95/31728 | 11/1995 | WIPO. |
| WO 96/01907 | 1/1996 | WIPO. |
| WO 96/06951 | 3/1996 | WIPO. |
| WO 96/08514 | 3/1996 | WIPO. |
| WO 96/12821 | 5/1996 | WIPO. |
| WO 96/13611 | 5/1996 | WIPO. |

OTHER PUBLICATIONS

Sanger F., S. Nicklen and A.R. Coulson (Dec. 1977) "DNA sequencing with chain-terminating inhibitors" vol. 74, No. 12 *Proc. Natl. Sci. USA* pp. 5463–5467.

Wallace R.B., et al. (1979) "Hybridization of synthetic oligodeoxyribonucleotides to $\Phi_x$ 174 DNA: the effect of single base pair mismatch" vol. 6, No. 11 *Nucleic Acids Research* pp. 3543–3557.

Coll P., K. Phillips, and F. C. Tenover (Oct. 1989) "Evaluation of a Rapid Method of Extracting DNA from Stool Samples for Use in Hybridization Assays" vol. 27, No. 10 *Journal of Clinical Microbiology* pp. 2245–2248.

Jessup J. M. and G. E. Gallick (Sep./Oct. 1992) "The Biology of Colorectal Carcinoma" *Current Problems in Cancer* pp. 263–328.

(List continued on next page.)

*Primary Examiner*—Nancy Degen
*Assistant Examiner*—Irem Yucel
*Attorney, Agent, or Firm*—Testa, Hurwitz & Thibeault, LLP

[57] ABSTRACT

The present invention provides methods for screening for the presence of a subpopulation of cancerous or precancerous cells in a heterogeneous cellular sample, such as a stool sample. The methods take advantage of the recognition that cellular debris from cancerous and precancerous cells is deposited onto only a longitudinal stripe of stool as the stool is forming in the colon. Accordingly, methods of the invention comprise obtaining a representative sample, such as a cross-sectional sample of stool in order to ensure that any cellular debris that is shed by colonic cells is obtained in the sample.

14 Claims, 4 Drawing Sheets

OTHER PUBLICATIONS

Litia A., L. Liukkonen and H. Siitari (1992) "Simultaneous detection of two cystic fibrosis alleles using dual-label time-resolved fluorometry" 6 *Molecular and Cellular Probes* pp. 505–512.

Young G.P., and B. H. Demediu (1992) "The genetics, epidemiology, and early detection of gastrointestinal cancers" 4 *Current Opininon in Oncology* pp. 728–735.

Hoss M., et al. (Sep. 17, 1992) "Excrement analysis by PCR" *Scientific Correspondence* pp. 199.

Sidransky, et al. (Apr. 3, 1992) "Identification of ras Oncogene Mutations in the Stool of Patients with Curable Colorectal Tumors" vol. 256 *Science* pp. 102–105.

Takeda S., S. Ichii, and Y. Nakamura (1993) "Detection of K-ras Mutation in Sputum by Mutant-Allele-Specific Amplification (MASA)" 2 *Human Mutation* pp. 112–117.

Leong P. K., et al. (1993) "Detection of MYCN Gene Amplification and Deletions of Chromosome 1p in Neuroblastoma by In Situ Hybridization Using Routine Histologic Sections" vol. 69, No. 1 *Laboratory Investigations* pp. 43–50.

Thibodeau S.N., G. Bren, D. Schaid (May 7, 1993) "Microsatellite Instability in Cancer of the Proximal Colon" vol. 260 *Science* pp. 816–819.

Naber S. P.(Dec. 1, 1994) "Molecular Pathology—Detection of Neoplasia" 331 *New England Journal of Medicine* pp. 1508–1510.

Cave H., et al. (1994) "Reliability of PCR Directly from Stool Samples: Usefulness of an Internal Standard" vol. 16, No. 5 *BioTechniques* pp. 809–810.

Caldas C., et al (Jul. 1, 1994) "Detection of K-ras Mutations in the Stool of Patients with Pancreatic Adenocarcinoma and Pancreatic Ductal Hyperplasia" 54 *Cancer Research* pp. 3568–3573.

Charlesworth B., P. Sniegowski and W. Stephan (Sep. 15, 1994) "The evolutionary dynamics of repetitive DNA in eukaryotes" vol. 371 *Nature* pp. 215–220.

Fearon E. R.(1995) "16 Molecular Abnormalities in Colon and Rectal Cancer" *The Molecular Basis of Cancer* pp. 340–357.

Ravelingien N., J. C. Pector & T. Velu (1995) "Contribution of molecular oncology in the detection of colorectal carcinomas" 58 *Acta Gastro–Enterologica Belgica* pp. 270–273.

Duffy M.J.(1995) "Can Molecular Markers Now Be Used for Early Diagnosis of Malignancy?" 41/10 *Clin. Chem.* pp. 1410–1413.

Blum H.E.(1995) "Colorectal Cancer: Future Population Screening for Early Colorectal Cancer" vol. 31A *European Journal of Cancer*, pp. 1369–1372.

Ridanpaa M., S. Anttila and K. Husgafvel–Pursiainen (1995) "Detection of Loss of Heterozygosity in the p53 Tumor Suppressor Gene Using a PCR–based Assay" 191 *Path. Res. Pract.* pp. 399–402.

Smith–Ravin, J., J. England, I.C. Talbot, W. Bodmer (1995) "Detection of c–Ki–ras mutations in faecal samples from sporadic colorectal cancer patients" 36 *Gut* pp. 81–86.

Orlow I., et al. (Oct. 18, 1995) "Deletion of the p16 and p15 Genes in Human Bladder Tumors" vol. 87, No. 20 *Journal of the National Cancer Institute* pp. 1524–1529.

Hasegawa, Y., et al., (1995) "Detection of K–ras mutations in DNAs isolated from feces of patients with colorectal tumors by mutant–allele–specific amplification (MASA)" 10 *Oncogene* pp. 1441–1445.

Loktionov A. and I. K. O'Neill (1995) "Early detection of cancer–associated gene alterations in DNA isolated from rat feces during intestinal tumor induction with 1,2–dimethylhydrazine" 6 *International Journal of Oncology* pp. 437–445.

Honchel R., K. C. Halling and S. N. Thibodeau (1995) "Genomic instability in neoplasia" vol. 6 *Seminars in Cell Biology* pp. 45–52.

Deuter R., S. Pietsch, S. Hertel and O. Muller (1995) "A method for preparation of fecal DNA suitable for PCR" vol. 23, No. 18 *Nucleic Acids Research* pp. 3800–3801.

Dib C., et al. (Mar. 14, 1996) "A comprehensive genetic map of the human genome based on 5,264 microsatellites" vol. 380 *Nature* pp. 152–154.

Cunningham C. and M.G. Dunlop (1996) "Molecular genetic basis of colorectal cancer susceptibility" 83 *British Journal of Surgery* pp. 321–329.

Mao L., et al. (Feb. 2, 1996) "Molecular Detection of Primary Bladder Cancer by Microsatellite Analysis" vol. 271 *Science* pp. 659–662.

Villa E., (May 1996) "Identification of Subjects at Risk for Colorectal Carcinoma Through a Test Based on K–ras Determination in the Stool" vol. 110, No. 5 *Gastroenterology* pp. 1346–1353.

Nollau P., C. Moser, G. Weinland, and C. Wagener (1996) "Detection of K–ras Mutations in Stools of Patients with Colorectal Cancer by Mutant–enriched PCR" 66 *Int. J. Cancer* pp. 332–336.

Eguchi S., N. Kohara, K. Komuta, and T. Kanematsu (Apr. 15, 1966) "Mutations of the p53 Gene in the Stool of Patients with Resectable Colorectal Cancer" vol. 77, No. 8 *Cancer Supplement* pp. 1707–1710.

Nollau P., C. Moser, and C. Wagener (May 1996) "Isolation of DNA from Stool and Bodily Fluids for PCR Amplication" vol. 20, No. 5 *BioTechniques* pp. 784–788.

Rhyu M. S. (Mar. 6, 1996) "Molecular Mechanisms Underlying Hereditary Nonpolyposis Colorectal Carcinoma" vol. 88, No. 5 *Journal of the National Cancer Institute* pp. 240–251.

Gyllensten U. B., Allen M. (1995) "Sequencing of In Vitro Amplified DNA" *Recombinant DNA Methodology II* (Wu, ed) pp. 565–578.

Smith–Ravin, et al., Jan. 1995, Gut, vol. 36, No. 1, pp. 81–86.

Sidransky, D., et al., 1992, Science, vol. 256, pp. 102–105.

1:           3'ACGCTACGG5'
2:    5'....ATCGGCTTACTGCGATGCC....3'

M

3:    3'....TAGCCGAATGACGCTACGG....5'
4:       5'ATCGGCTTA3'

1:           3'ACGCTACGG5'
2:    5'....ATCGGCTTATTGCGATGCC....3'

F

3:    3'....TAGCCGAATAACGCTACGG....5'
4:       5'ATCGGCTTA3'

METHODS FOR DETECTING COLON CANCER FROM STOOL SAMPLES

This application claims priority under 35 U.S.C. §119(e) to provisional application Ser. No. 60/10,856, filed on Jan. 30, 1996.

FIELD OF THE INVENTION

This invention relates to methods for the early detection of colon cancer in patients and more particularly to methods for preparing stool samples for the detection of colon cancer so as to assure or increase the likelihood that the sample will contain the diagnostically relevant information if the patient has a cancerous or precancerous lesion, and to methods for stool sample analysis.

BACKGROUND OF THE INVENTION

Stool samples frequently must be prepared for medical diagnostic analysis. Stool samples may be analyzed to help diagnose medical conditions ranging from parasitic, bacterial or viral infections to inflammatory bowel disease and colorectal cancer.

Colorectal cancer is a leading cause of death in Western society. However, if diagnosed early, it may be treated effectively by surgical removal of the cancerous tissue. Colorectal cancers originate in the colorectal epithelium and typically are not extensively vascularized (and therefore not invasive) during the early stages of development. Colorectal cancer is thought to result from the clonal expansion of a single mutant cell in the epithelial lining of the colon or rectum. The transition to a highly vascularized, invasive and ultimately metastatic cancer which spreads throughout the body commonly takes ten years or longer. If the cancer is detected prior to invasion, surgical removal of the cancerous tissue is an effective cure. However, colorectal cancer is often detected only upon manifestation of clinical symptoms, such as pain and black tarry stool. Generally, such symptoms are present only when the disease is well established, often after metastasis has occurred, and the prognosis for the patient is poor, even after surgical resection of the cancerous tissue. Early detection of colorectal cancer therefore is important in that detection may significantly reduce its morbidity.

Invasive diagnostic methods such as endoscopic examination allow for direct visual identification, removal, and biopsy of potentially cancerous growths such as polyps. Endoscopy is expensive, uncomfortable, inherently risky, and therefore not a practical tool for screening populations to identify those with colorectal cancer. Non-invasive analysis of stool samples for characteristics indicative of the presence of colorectal cancer or precancer is a preferred alternative for early diagnosis, but no known diagnostic method is available which reliably achieves this goal.

Current non-invasive diagnostic methods involve assaying stool samples for the presence of fecal occult blood or for elevated levels of carcinoembryonic antigen, both of which are suggestive of the presence of colorectal cancer. Additionally, recent developments in molecular biology provide methods of great potential for detecting the presence of a range of DNA mutations or alterations associated with and indicative of the presence of colorectal cancer. The presence of such mutations theoretically can be detected in DNA found in stool samples during the early stages of colorectal cancer. However, stool comprises cells and cellular debris from the patient, from microorganisms, and from food, resulting in a heterogeneous population of cells. This makes detection of a small, specific subpopulation impossible to detect reliably.

Stool diagnostic assays for colorectal cancer described in the art typically are performed on samples prepared from randomly sampled portions of voided stool. However, samples prepared according to such methods do not reproducibly yield characteristics indicative of the presence of colorectal cancer or precancer, even when prepared from stool voided by a patient with colorectal cancer or precancer. There is therefore a need in the art for methods for early diagnosis of colorectal cancer or precancer that will reproducibly detect characteristics indicative of the presence of cancerous or precancerous material in samples prepared from stool voided by a patient with colorectal cancer or precancer. Such methods are provided herein.

SUMMARY OF THE INVENTION

Figure 1:
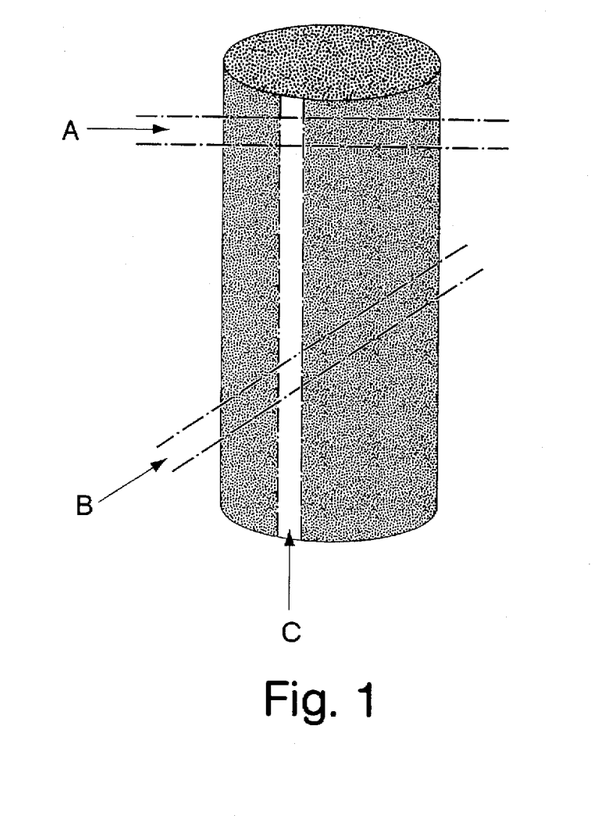
FIG. 1 is a diagram of a cylinder which represents a formed stool and shows various cross-sections which will contain material from the entire circumference of a stool. The Section labeled "A" is a typical coronal section and the section labeled "B" is a typical sagittal section. The strip labeled "C" represents material shed from cancerous tissue which is deposited in a longitudinal stripe.

It has now been appreciated that cells and cellular debris are shed from colonic epithelial cells onto forming stool in a longitudinal "stripe" of material along the length of the stool. The shed material is confined to this longitudinal stripe, as shown in FIG. 1 (designated "C"). Based upon this recognition, Applicants teach that stool sample preparation for diagnostic testing must include taking a representative sample in order to ensure that the sample will contain any cells or cellular debris that was shed into the stool as it passed through the colon. Accordingly, methods of the invention comprise obtaining at least a cross-sectional portion of stool voided by a patient, and performing an assay to detect in the sample the presence of cells or cellular debris shed from epithelial cells lining the colon that may be indicative of cancer or precancer. Most often such cells will be derived from a polyp or a cancerous or precancerous lesion at a discrete location along the colon. For purposes of the present invention, a precancerous lesion comprises precancerous cells, and precancerous cells are cells that have a mutation that is associated with cancer and which renders such cells susceptible to becoming cancerous. As shown in FIG. 1, a cross-sectional sample is a sample that contains at least an entire circumference of the stool (or portion of a stool comprising an entire cross-sectional portion), as, for example, in a coronal section or a sagittal section.

In a preferred embodiment, methods of the invention comprise the steps of obtaining at least a cross-sectional portion of a stool voided by a patient, and performing an assay to detect debris from a clonal population of transformed cells. The transformed cells comprise, for example, a clonal subpopulation of cells having one or more mutations (for purposes of the present application, a mutation is a deletion, substitution, addition, modification, intercalation or rearrangement of DNA). Preferred methods of the invention comprise detection of characteristics of such transformed cells, including, for example, mutations, proteins expressed uniquely or in altered amounts in transformed cells, and blood. Particularly preferred methods of the invention comprise obtaining at least a cross-sectional portion of a stool sample, and performing an assay to detect DNA characteristics indicative of the presence of a clonal subpopulation of cells in the sample. The clonal subpopulation may be, for example, a subpopulation of cancerous or precancerous cells, having a mutation in, for example, a p53 tumor suppressor gene. Clonal subpopulations of cells detected by methods according to the invention are often characterized by a massive loss of DNA, resulting in a loss of heterozygosity that renders ineffective the gene or genes encompassed by the deletion.

Methods of the invention also comprise obtaining a representative (i.e., cross-sectional) sample of stool and homogenizing the stool in a buffer, such as a buffer comprising a detergent and a proteinase and optionally a DNase inhibitor.

In methods according to the invention, an assay performed on at least a cross-sectional portion of stool may be an assay to detect the presence of elevated levels of carcinoembryonic antigen shed from cells lining the colon. Such an assay may also comprise detecting the presence of occult blood. However, methods of the invention preferably comprise an assay wherein the sample is exposed to an antibody that specifically binds to a molecule characteristic of cellular debris shed from cells comprising a subpopulation of cells having a mutation that is potentially associated with cancer.

Methods of the invention are especially and most preferably useful for detecting DNA characteristics indicative of a subpopulation of transformed cells in a representative stool sample. The DNA characteristics may be, for example, mutations, including loss of heterozygosity, microsatellite instability, and others. An assay for DNA characteristics in a method of the invention may comprise the step of determining whether a difference exists in a number X of a first allele known or suspected to be mutated in a subpopulation of cells in a representative stool sample, and a number Y of an allele known or suspected not to be mutated in the sample, a statistically-significant difference being indicative of a mutation and the possible presence of cancer in a subpopulation of cells in the sample. In an embodiment of the invention, the difference between a number of a tumor suppressor gene and a number of a non-cancer-associated gene are compared, a statistically-significant difference in the numbers being indicative of a mutation in the tumor suppressor gene.

Assays useful in the practice of methods according to the invention also include an assay to detect the presence of a deletion or other mutation in a region encompassing a polymorphic nucleotide. In such an assay, a number of a polymorphic nucleotide present at maternal and paternal alleles, wherein the patient is heterozygous for the polymorphic nucleotide, is determined. A statistically significant difference between a number of a polymorphic nucleotide in a maternal allele and a paternal allele is indicative of the presence of a deletion in one of the two alleles.

Methods of the invention typically include, following sample preparation and an assay for characteristics of cells or cellular debris, a visual examination of the colon in order to determine if a polyp or other lesion is, in fact, present. Finally, surgical resection of abnormal tissue may be done in order to prevent the spread of cancerous or precancerous tissue.

Accordingly, methods of the invention provide means for screening for the presence of a cancerous or precancerous subpopulation of cells in a heterogeneous sample, such as a stool sample. Methods of the invention reduce morbidity and mortality associated with lesions of the colonic epithelium. Moreover, methods of the invention comprise more accurate screening methods than are currently available in the art, because current methods take advantage of the observation that cancerous or precancerous cells shed debris only onto or into part of the surface of the forming stool. The present methods reliably assay over the entire circumference of the stool, thereby increasing the likelihood of detecting an abnormality if one exists. Further aspects and advantages of the invention are contained in the following detailed description thereof.

DETAILED DESCRIPTION OF THE INVENTION

Methods according to the present invention are useful for the preparation of stool samples that will reproducibly contain cells or cellular debris shed from a clonal population of cancerous or precancerous cells, if such a population is present at any site along the colon of a patient. These samples are then used to perform assays to detect characteristics indicative of cancer in a highly-reproducible and accurate way. Such methods provide an improvement over the art inasmuch as they teach removing at least a cross-sectional sample from a stool voided by a patient. Without the recognition that at least a cross-sectional sample must be obtained, there is no means for reproducibly obtaining a sample that will contain a cancerous or precancerous subpopulation of cells, if one exists.

Methods described in the art do not recognize that, unlike infection by parasites, bacteria and viruses, characteristics indicative of the presence of colon cancer, especially early stage colon cancer, are found only in a specific portion of voided stool. If the sampled portion of stool does not include the portion that happens to contain cells and cellular debris shed from early-stage cancer tissue, the diagnostic assay necessarily will fail to detect the characteristics indicative of the presence of colorectal cancer in a reliable manner even if homogenized, i.e., will produce a false-negative result.

Sloughed cells from, for example, a polyp forming in the epithelial lining of the colon, or on early stage cancerous lesions, are sloughed onto only the portion of the forming stool that comes into contact with the polyp or lesion. Accordingly, in early stage disease, only a small portion of the surface layer of the forming stool will contain sloughed cells, and if that portion happens not to be taken as part of the sample, an assay for indicia of colon cancer necessarily will produce a false-negative result. A brief review of the anatomy and physiology of the colon will aid in an understanding of this phenomenon.

A typical adult colon is approximately six feet in length, with a diameter of about two to three inches. Numerous bends and folds are present throughout its length. The colon removes water from liquid or semi-liquid waste material that enters the colon, and relatively solid stool begins to form in the proximal third of the colon. Epithelial cells line the lumen of the colon, and the lumenal surface is organized into microscopic crypts. Colorectal epithelial cells are replaced every four to five days. The epithelial cells divide rapidly at the base of the crypts and migrate to the apeces, where cells appear to undergo apoptosis (programmed cell death), and cellular debris is shed into the lumen. The lining of the colorectal lumen is elastic and the diameter of the lumen is determined by the volume of stool that is passing through the colon at any given time. As a result, the surface of the forming stool passing through the colon is in direct contact with the epithelial lining of the lumen. Shed epithelial cells (which may or may not have undergone apoptosis) and cellular debris therefore are incorporated onto the surface of stool as it passes through the colon.

Cells and cellular debris from colorectal epithelial cancers therefore also are shed onto forming stool. Most colorectal cancers develop in regions of the colon where stool is relatively solid, indeed approximately one third of such cancers develop in the rectum. Markers indicative of the presence of cancer, including cells, cellular debris, DNA, blood, and carcinoembryonic antigen, are shed onto the portion of the forming stool that contacts the cancerous tissue as the stool passes through the colon. Since the stool is relatively solid, these markers will remain on or near the surface of the stool where they were deposited and will not be homogeneously dispersed throughout the stool. As stool passes over a cancerous or precancerous growth, material from the growth will be deposited along the stool, but only on the part of the stool circumference that comes into direct contact with the cancerous or precancerous tissue comprising the lesion. Stool voided by a patient with colorectal cancer or precancer is therefore characterized by a longitudinal "stripe" of diagnostically relevant material derived from the cancerous or precancerous tissue.

A sample that does not include material from the entire circumference of a stool voided by a patient with colorectal cancer or precancer will not reproducibly contain material derived from the cancerous or precancerous tissue. Currently, random, non-cross-sectional samples ("smears") of voided stool are analyzed in clinical settings. In these, sloughed cancerous or precancerous cells and cellular debris have no possibility of detection unless the sample happens by chance to contain the portion of stool which made contact with the region of the colon from which cells were sloughed.

Furthermore, cancers typically develop by clonal expansion of a single mutant cell, and in the early stages of the disease, i.e., when surgical removal is an effective cure, the cancerous lesion will be very small and may lie on a small arc of the circumference of the colon. Material derived from such an early stage cancer therefore will be shed onto or into stool in a very narrow stripe (labeled C in FIG. 1). Consequently, a sample that does not contain the entire circumference of a stool voided by a patient with early stage colorectal cancer or precancer only by chance will contain material indicative of the presence of the early stage cancerous or precancerous condition. However, early detection of colorectal cancer is very important for effective surgical intervention. The present invention provides methods for reproducible early detection of characteristics indicative of the presence of cancer or precancer in a patient.

Analysis of at least a cross-sectional sample of stool (including a whole stool), as shown in FIG. 1, ensures that at least a portion of cells and cellular debris shed from any existing cancerous or pre-cancerous cells (even if shed from small early stage cancerous or pre-cancerous tissue, e.g., small polyps) will be present in the portion of the stool sample to be analyzed. Indeed taking at least a cross-section of the stool sample avoids the possibility of analyzing stool portions that will not contain sloughed cancerous or precancerous cells even when the patient has colorectal cancer or precancer.

Once a cross-sectional stool sample is obtained, it may be homogenized by known methods to distribute cells and cellular debris throughout the sample. An assay then is performed on the homogenate, or an extract of the homogenate, to detect the presence of cells and/or cellular debris in the sample. The assay may be any one or a combination of histological cellular assays, antibody based immunoassays (or other formats) designed to detect the presence of a molecule characteristic of transformation such as a protein, or DNA-based assays for detecting mutations or genetic characteristics indicative of colorectal cancer. Known assay protocols, those disclosed herein or in copending application serial number Co-owned U.S. patent application, Ser. No. 08/700,583 or assays hereafter developed may be used in the practice of the invention. Non-limiting examples of useful known assay protocols include those disclosed in U.S. Pat. No. 5,137,806 (detection of sequences in selected DNA molecules), U.S. Pat. No. 5,348,855 (assay for nucleic acid sequences), U.S. Pat. No. 5,512,441 (detection of mutant alleles), U.S. Pat. No. 5,272,057 and U.S. Pat. No. 5,380,645 (RFLP analysis), U.S. Pat. No. 5,527,676 (detection of p53 gene sequences), U.S. Pat. No. 5,330,892 (detection of MCC gene sequences), U.S. Pat. No. 5,352,775 (detection of APC gene sequences), U.S. Pat. No. 5,532,108 (detection of DCC gene sequences), and in WO96/08514 (monoclonal antibodies against human colon carcinoma-associated antigens), the disclosures of each of which are incorporated by reference herein. Alternatively, or additionally, an assay for fecal occult blood may be performed as reported in U.S. Pat. Nos. 4,333,734 and 5,196,167, incorporated by reference herein. Assays useful in the context of the present invention also include an assay for carcinoembryonic antigen as reported in U.S. Pat. No. 5,380,647, incorporated by reference herein. Finally, the sample may be prepared, as reported in U.S. Pat. No. 4,857,300, incorporated by reference herein, for histological examination to detect characteristics indicative of the presence of cancerous or precancerous cells.

The purpose of any assay protocol used in connection with obtaining at least a cross-sectional sample is to identify candidates for subsequent invasive diagnostic procedure such as colonoscopy or sigmoidoscopy. The assay accordingly need not definitively detect the presence of a cancerous or precancerous lesion, although false negatives obviously are to be avoided. The goal of the test protocol is not to determine whether in the vast quantities of cell debris in the sample there are a few cells which bear a mutation commonly associated with early stage transformation, but rather whether the sample contains debris indicative of clonal expansion of a mutant cellular subpopulation. Maximum benefit will come from an assay designed to detect the likely presence of a clonally expanded cell population, i.e., of transformed colonic epithelial cells which comprise the cancerous or precancerous lesions. Assays having the ability to detect cancer or precancer in early stages are preferred in methods of the invention. Assays using polymerase chain reaction (PCR), restriction fragment length polymorphism (RFLP) or other methods for nucleic acid analysis may be used to detect known DNA characteristics indicative of the presence of colorectal cancer or precancer. More precise methods for quantitative detection of cellular debris, such as DNA fragments or segments, may be used to analyze cross-sectional samples according to methods described herein.

A preferred assay interrogates the sample for DNA characteristics indicative of the development of cancer or precancer. However, assays for use with methods of the invention may detect any abnormal cellular debris shed from clinically-relevant transformed tissue. Thus, in accordance with a preferred aspect of the invention, an assay is used to detect the presence of characteristics of cells which have experienced loss of heterozygosity, microsatellite instability or other mutation.

The following examples provide details of methods according to the invention. However, numerous additional aspects of the invention, especially in terms of assays to be performed, will become apparent upon consideration of the following detailed description thereof.

EXAMPLE 1

Preparation of a Stool Sample

A sample is prepared such that it contains at least a cross-sectional portion of a stool voided by a patient. The cross-sectional portion is removed from the voided stool by making one or more sagittal or coronal section through the stool, as shown in FIG. 1. The removed portion comprises material from the entire circumference of the stool. Alternatively a whole stool may be used. The portion contains sufficient material to allow subsequent diagnostic assays to be performed. Stool is voided into a receptacle that is preferably small enough to be transported to a testing facility. The receptacle may be fitted to a receptacle may be fitted to a conventional toilet such that the receptacle accepts stool voided in a conventional manner. The receptacle may comprise a mesh or screen of sufficient size and placement such that stool is retained while urine is allowed to pass through the mesh or screen and into the toilet. The receptacle additionally may comprise means for removing a cross-sectional portion from the stool. Moreover, the receptacle may comprise means for introducing homogenization buffer or one or more preservatives, such as alcohol, a solution of high salt concentration, antibiotics, and chaotropic salts in order to neutralize bacteria present in the stool sample. The homogenization buffer may be a physiologically compatible buffer such as phosphate buffered saline, and may comprise salt such as 20–100 mM NaCl or KCl. The homogenization buffer may also comprise a detergent, such as 1–10% SDS or triton, and/or a proteinase, such as proteinase K. The buffer may also contain inhibitors of DNA and RNA degrading enzymes.

Figure 2:
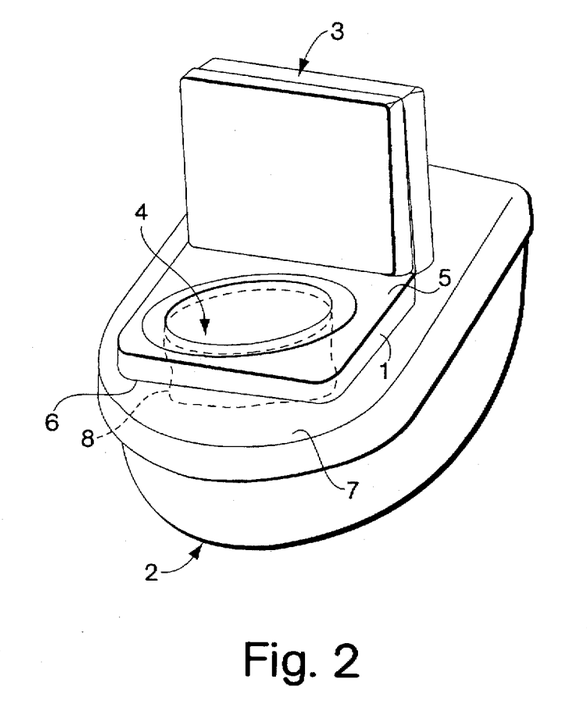
FIG. 2 is a schematic diagram of a receptacle for containing a stool sample.

The receptacle, whether adapted to fit a toilet or simply adapted for receiving the voided stool sample, should include sealing means sufficient to contain the voided stool sample and any solution added thereto and to prevent the emanation of odors. An exemplary receptacle is shown in FIG. 2. A shown in that figure, the receptacle has a support frame 1 which is placed directly over the toilet bowl 2. The support frame 1 has attached thereto an articulating cover 3 which may be placed in a raised position, as shown in FIG. 2, for depositing of sample or a closed position (not shown) for sealing voided stool within the receptacle. The support frame 1 additionally has a central opening 4 traversing from a top surface 5 through to a bottom surface 6 of the support frame 1. The bottom surface 6 directly communicates with a top surface 7 of the toilet 2. Extending from the bottom surface 6 of the support frame 1 is a means 8 for capturing voided stool. Means 8 may be fixedly attached to the support frame 1 or may be removably attached for removal subsequent to deposition of stool. Means 8 may comprise a further means for removing at least a cross-sectional portion from the voided stool. A preferable sample size is at least 5–10 g or at least 5–10 ml. A means to assess the presence of a minimal sample size may comprise a physical diagram indicating the minimal sample size. Alternatively a means to assess the presence of a minimal sample size may comprise the displacement of a liquid or of a mechanical device to a minimal level upon deposit of the stool sample.

Once obtained, the cross-sectional stool sample is homogenized in an appropriate buffer, such as phosphate buffered saline. Homogenization means and materials for homogenization are generally known in the art. Thus, particular homogenization methods may be selected by the skilled artisan and may depend upon the assay to be employed. The buffer may contain detergent, salt, proteinase, inhibitors of DNA and RNA degrading enzymes. The composition of the buffer will depend on the type of assay to be performed. If a fecal occult blood assay is to be performed, the buffer may contain chemical compounds which react with blood to produce a color, the intensity of which can be measured. Buffers useful for detecting the presence of fecal occult blood are known in the art. If a test is to be performed for the presence of a particular protein, the buffer should not contain a proteinase capable of degrading such tumor marking antigens.

DNA or RNA may be isolated from the homogenate using methods known in the art. Subsequent tests may be performed on the isolated DNA and RNA.

EXAMPLE 2

Exemplary Enumerative methods for Detection of Colorectal Cancer or Precancer in stool samples DNA characteristics associated with the presence of colorectal cancer or a precancerous lesion may be detected in stool samples prepared according to the invention, using, for example, the methods described in the following sections. A careful endoscopic examination preferably is performed on positive Individuals, followed by early surgical excision of any diseased tissue.

A. Reference-Target

Methods of the invention are used to prepare a stool sample followed by detection of a deletion or other mutation in the p53 tumor suppressor gene. The p53 gene is a good choice because a loss of heterozygosity in p53 is often associated with colorectal cancer. An mRNA sequence corresponding to the DNA coding region for p53 is reported as GenBank Accession No. M92424. At least a cross-section of a voided stool sample is obtained and prepared according to methods of the invention as described immediately above. The sample need not be further processed for analysis. However, DNA or RNA may optionally be isolated from the sample according to methods known in the art. See, Smith-Ravin, et al., *Gut*, 36:81–86 (1995), incorporated by reference herein.

Nucleic acids may be sheared or cut into small fragments by, for example, restriction digestion. The size of nucleic acid fragments produced is not critical, subject to the limitations described below. A target allele that is suspected of being mutated (p53 in this example) and a reference allele are chosen. A reference allele may be any allele known normally not to be mutated in colon cancer.

Either portions of a coding strand or its complement may be detected. For exemplification, detection of the coding strand of p53 and reference allele are described herein. Complement to both p53 and reference allele are removed by hybridization to anti-complement oligonucleotide probes (isolation probes) and subsequent removal of duplex formed thereby. Methods for removal of complement strands from a mixture of single-stranded oligonucleotides are known and include techniques such as affinity chromatography. Upon converting double-stranded DNA to single-stranded DNA [See, e.g., Sambrook, et al., *Molecular Cloning, A Laboratory Manual* (1989) incorporated by reference herein], sample is passed through an affinity column packed with bound isolation probe that is complementary to the sequence to be isolated away from the sample. Conventional column chromatography is appropriate for isolation of complement. An affinity column packed with sepharose or other appropriate materials with attached complementary nucleotides may be used to isolate complement DNA in the column, while allowing DNA to be analyzed to pass through the column. See Sambrook, Supra. As an alternative, isolation beads may be used to exclude complement as discussed in detail below.

After removal of complement strands, first oligonucleotide probes which hybridize to at least a portion of the p53 allele and second oligonucleotide probes that hybridize to at least a portion of the reference allele are obtained. The probes are labeled with a detectable label, such as fluorescein or with detectable particles. Distinct labels for the probes are preferred. However, identical labels may be used if, for example, sample is assayed in two separate aliquots. Probes may be labeled with identical or with distinct labels. However, distinct labels are preferred.

Labeled probes then are exposed to sample under hybridization conditions. Such conditions are well-known in the art. See, e.g., Wallace, et al., *Nucleic Acids Res.*, 6:3543–3557 (1979), incorporated by reference herein. First and Second oligonucleotide probes that are distinctly labeled (i.e. with different radioactive isotopes, fluorescent means, or with beads of different size, See infra) are applied to a single aliquot of sample. After exposure of the probes to sample under hybridization conditions, sample is washed to remove any unhybridized probe. Thereafter, hybridized probes are detected separately for p53 hybrids and reference allele hybrids. Standards may be used to establish background and to equilibrate results. Also, if differential fluorescent labels are used, the number of probes may be determined by counting differential fluorescent events in a sample that has been diluted sufficiently to enable detection of single fluorescent events in the sample. Duplicate samples may be analyzed in order to confirm the accuracy of results obtained.

If there is a statistically-significant difference between the amount of p53 detected and the amount of the reference allele detected, it may be assumed that a mutation has occurred in p53 so as to alter its sequence and prevent hybridization of the probe, or that at least a portion of the region of the genome containing p53 has been lost in a subpopulation of cells shed from the colon. The patient therefore may be at risk for developing or may have developed colon cancer. Statistical significance may be determined by any known method. See, e.g., Steel, et al., *Principles and Procedures of Statistics: A Biometrical Approach* (McGraw, Hill, 1980). Statistical methods are also outlined in co-owned patent application, Ser. No. 08/700,583.

The determination of a p53 mutation allows a clinician to recommend further treatment, such as endoscopy procedures, in order to further diagnose and, if necessary, treat the patient's condition. The following examples illustrate methods that allow direct quantification of hybridization events.

1. Method for Quantitation of Target and Reference Polynucleotides

Enhanced quantification of binding events between hybridization probes and target or reference is accomplished by coupling hybridization probes to particles, such as beads (hybridization beads). In order to obtain a precise quantitative measure of the amount of a polynucleotide in a sample, hybridization beads are constructed such that each bead has attached thereto a single oligonucleotide probe.

a. Method for Preparation of Probe-Bead Combinations

A single probe is attached to a bead by incubating a large excess of hybridization beads with oligonucleotide probes of a given type (i.e., either first or second oligonucleotide probes). Coupling of probe to bead is accomplished using an affinity-binding pair. For example, beads may be coated with avidin or streptavidin and probes may be labeled with biotin to effect attachment of the probe to the bead. The mixture of beads and probes is agitated such that 100% of the probes are bound to a bead. The mixture is then exposed to a matrix, such as an affinity column or a membrane coated with oligonucleotides that are complementary to the probe. Only beads that have an attached probe will adhere to the matrix, the rest being washed away. Beads with coupled probe are then released from the matrix by melting hybridizations between probe and complement. Multiple exposures to the matrix and pre-washing of the column reduces non-specific binding. Moreover, naked beads (i.e., without attached probe) may be exposed to the matrix to determine a background number of beads that can be expected to attach to the matrix in the absence of probe.

By using a vast excess of beads relative to probe as described above, the vast majority of recovered beads will have only one attached probe. For example, if a mixture has a ratio of 1 probe to 1000 beads, it is expected that only about 1 bead in a million will have two attached probes and even less than one bead in a million will have more than two attached probes. Accordingly, hybridization beads are provided in an effective 1:1 ratio with probe which allows for precise quantification of target and reference polynucleotide as described below.

For each assay described below, two distinct hybridization beads are used. A first hybridization bead has attached thereto a single first oligonucleotide probe that is complementary to at least a portion of a target polynucleotide (e.g., a p53 allele). A second hybridization bead, of a size distinct from the first hybridization bead, has attached thereto a single second oligonucleotide probe that is complementary to at least a portion of a reference polynucleotide (i.e., one that is known or suspected not to be mutated in the sample).

b. Use of Beads to Quantify Target and Reference Polynucleotides

DNA is melted (denatured to form single-stranded DNA) by well-known methods See, e.g., Gyllensten, eta., in *Recombinant* DNA Methodology II, 565–578 (Wu, ed., 1995), incorporated by reference herein. One may detect either a coding strand or its complement in order to quantify target and/or reference polynucleotide. For purposes of illustration, the present example assumes detection of the coding strand.

2. Removal of Complement

Single-stranded complement of the target polynucleotide (e.g., p53) and reference polynucleotide are removed from the sample by binding to oligonucleotide probes that are complementary to target or reference complement. Such probes, referred to herein as isolation probes, are attached to isolation beads prior to their introduction into the sample.

The beads may be magnetized. Thus, when magnetized isolation beads [with attached isolation probe(s)] are introduced into the sample, the attached isolation probes hybridize to complement of target or reference (or vice versa). Isolation beads preferably are introduced in vast excess in order to saturate complement binding. Once hybridization is complete, a magnetic field is applied to the sample to draw the magnetized isolation beads (both with and without hybridized complement) out of the sample. Assuming that a sufficient quantity of isolation beads are introduced into the sample, removal of the isolation beads effectively removes all target and reference complement from the sample.

In an alternative method for complement removal, an excess of oligonucleotide probe labeled with biotin is exposed to the melted or dehybridized (single stranded) sample under hybridization conditions. Once hybridization is complete, the sample is exposed to a column containing immobilized avidin. The biotin-labeled probe, whether free or hybridized to complement, is bound by avidin on the column. The remainder of the DNA, including target and reference coding strands to be detected, pass through the column. In contrast to the description of hybridization beads above, beads for removal of complement may each comprise multiple complementary oligonucleotide probes.

3. Quantitation of Target and Reference

Two sets of hybridization beads are prepared as described above. Each member of a first set of hybridization beads (all of which are identical to each other) has attached thereto a single oligonucleotide probe that is complementary to at least a portion of the target polynucleotide, i.e., the portion of the genome which is altered in the cells of a cancerous lesion. Each member of a second set of identical hybridization beads (all of which are identical to each other but not to the first set) has attached thereto a single oligonucleotide probe that is complementary to at least a portion of the reference polynucleotide, i.e., a portion of the genome which is not likely to be altered in malignant cells. Members of the second set of hybridization beads are of a size or color distinct from that of members of the first set of hybridization beads. First and second hybridization beads may also be distinguished on the basis of other characteristics. For example, beads may have fluorescent markers that are distinguished by their fluorescence wavelength. Beads with distinct electrochemical charges also may be used. The precise modality used for distinguishing beads is not essential as long as it is possible to distinguish between first and second probe on the basis of distinctions between attached first and second beads.

Both sets of hybridization beads are exposed to the sample under hybridization conditions thereby allowing hybridization to reference and target. The sample then is washed to remove unhybridized bead/probe combinations. Unhybridized bead/probe combinations are removed by, for example, passing the sample through a column lined of immobilized DNA complementary to the probe sequence. Thus, any unhybridized bead/probe combinations are retained on the column while duplex passes through. Subsequently, the sample is exposed to means for differentially counting hybridization beads in order to quantify first and second hybridization probes which have formed duplexes. The numbers obtained provide a precise estimate of the number of copies of the reference and target polynucleotide in the population because differential counting means count individual beads. One bead is equal to one probe which, in turn, signifies one copy of the nucleic acid being measured.

An example of a differential counting means is an impedance measuring device, such as a Coulter counter (Coulter Electronics, Inc., Miami, Fla.). Sample is passed through the device which differentially detects the two types of hybridization beads by measuring their differential impedance of an electric current. Alternatively, the device may measure fluorescence, color, or other parameters. In order to increase the speed of the assay, a multi-orifice device may be used. A multi-orifice impedance counter is shown schematically in FIG. 2. A multi-orifice array is placed at one end of a column filled with an electrically-conductive fluid, such as saline. Hybridization beads with either hybridized target or reference segments are inserted at an opposite end of the column. Each orifice is large enough to accommodate only one hybridization bead at a time and sufficiently wide to allow reliable impedance measurements. A voltage is set across each orifice. Each hybridization bead (which is nonconducting), as it passes through one of the orifices, displaces a volume of saline, thus creating an impedance that is proportional to its size. This, in turn, creates a measurable decrease in current that is directly correlated with the size of the bead. By compiling the number of each of the two distinct impedance events, a precise estimate of the number of hybridization beads and, therefore, the number of probes of each type in the population may be obtained.

Upon quantitative measurement of first and second hybridization beads, the data may be analyzed to determine whether any difference between the amounts of first and second hybridization beads is statistically significant. A reduction in the amount of target relative to the reference is indicative of a mutation in or deletion of the target allele in a subpopulation of cells in the sample. Where the p53 gene is the target allele, such a mutation is indicative of a cancerous or precancerous condition. A clinician may use such results as a basis for prescribing additional treatment, such as endoscopy and polypectomy procedures.

B. Detection of Mutations in Single-base Polymorphisms

The basic method described above may also be applied to detect a loss of heterozygosity or other mutation at a single base polymorphic site between maternal and paternal alleles. Such detection is typically an indication of a larger deletion or other mutation. However, a mutation at a single polymorphic nucleotide may be all that is necessary to inhibit gene function in one of the two alleles. A mutation in a single-base polymorphic region may be difficult to detect due to a recently-discovered phenomenon called complementary reduplication. In complementary reduplication, the loss of one of two alleles at a particular locus results in "reduplication" of the surviving allele. Reduplication usually takes place on the chromosome containing the surviving allele and involves the production of one or more copies of the surviving allele in close proximity on the chromosome to the position of the surviving allele. In the case of a locus that displays one or more single-base allelic polymorphisms (i.e., heterozygosity at the locus is determined by virtue of one or more single-base differences in one or more regions of the locus), complementary reduplication results in the insertion on the chromosome containing the surviving allele of a duplicate of the sequence corresponding to that which was deleted. Even under the most stringent hybridization conditions, some of a probe directed against the deleted sequence will bind to the reduplicated sequence at a locus of a single-base polymorphism. Accordingly, in such circumstances, the deletion may not be detected because any true difference in the number of probes binding to the polymorphic site (i.e., the allelic region encompassing the single-base polymorphism) may be obscured by an increase resulting from the other allele's reduplicated region.

The problems associated with complementary reduplication, and with non-specific probe binding generally, are alleviated by the practice of the methods described herein. Such methods allow detection of a deletion in one of two alleles present at a specific locus in a subpopulation of cells contained in a biological sample. Numerous alleles, including tumor suppressor alleles, contain single polymorphic nucleotides in the context of a constant nucleic acid region. Individuals normally may be either homozygous or heterozygous for the polymorphic nucleotide. Since numerous single-base polymorphic nucleotide sites exist in most alleles, the probability that a given individual is heterozygous at least one of the single-base polymorphism sites is high. A statistically-significant reduction in one of the two nucleotides at a single-base polymorphic site (at which the individual is heterozygous) may be used as a marker for a deletion in the allele encompassing that site.

Genomic regions containing known single-base polymorphisms may be identified by reference to a nucleotide database, such as GenBank, EMBL, or any other appropriate database. The existence of polymorphisms may be determined by methods taught herein, gel electrophoresis or by other standard methods. For purposes of the invention, a single-base polymorphism is intended to be a single polymorphic nucleotide adjacent to a non-polymorphic region of the allele regardless of whether the single polymorphic nucleotide forms part of a larger polymorphic site (i.e. the single-base polymorphism may be the terminal nucleotide of a larger, polynucleotide polymorphism). For cancer detection, the regions considered are regions in which loss of heterozygosity is prevalent, such as regions containing tumor suppressor genes. A given individual may be homozygous or heterozygous for the polymorphic nucleotide in any identified single-base polymorphic region. Accordingly, if a number of single-base polymorphic regions are identified, the probability increases that at least one heterozygous single-base polymorphic region is found in a sample.

Once single-base polymorphic sites are identified, a DNA sample is obtained from a patient, e.g., from blood cells, to determine which of those sites is heterozygous in normal (i.e., non-cancerous or non pre-cancerous) cells for that individual. Then, a stool sample is prepared as described above. Double stranded DNA in the sample is converted to single-stranded DNA. Then, either the coding strand or the anti-coding strand for both alleles is removed from the sample. As will be evident from the following discussion, methods disclosed herein are indifferent as to whether coding strand or anti-coding strand is tested.

Figure 3:
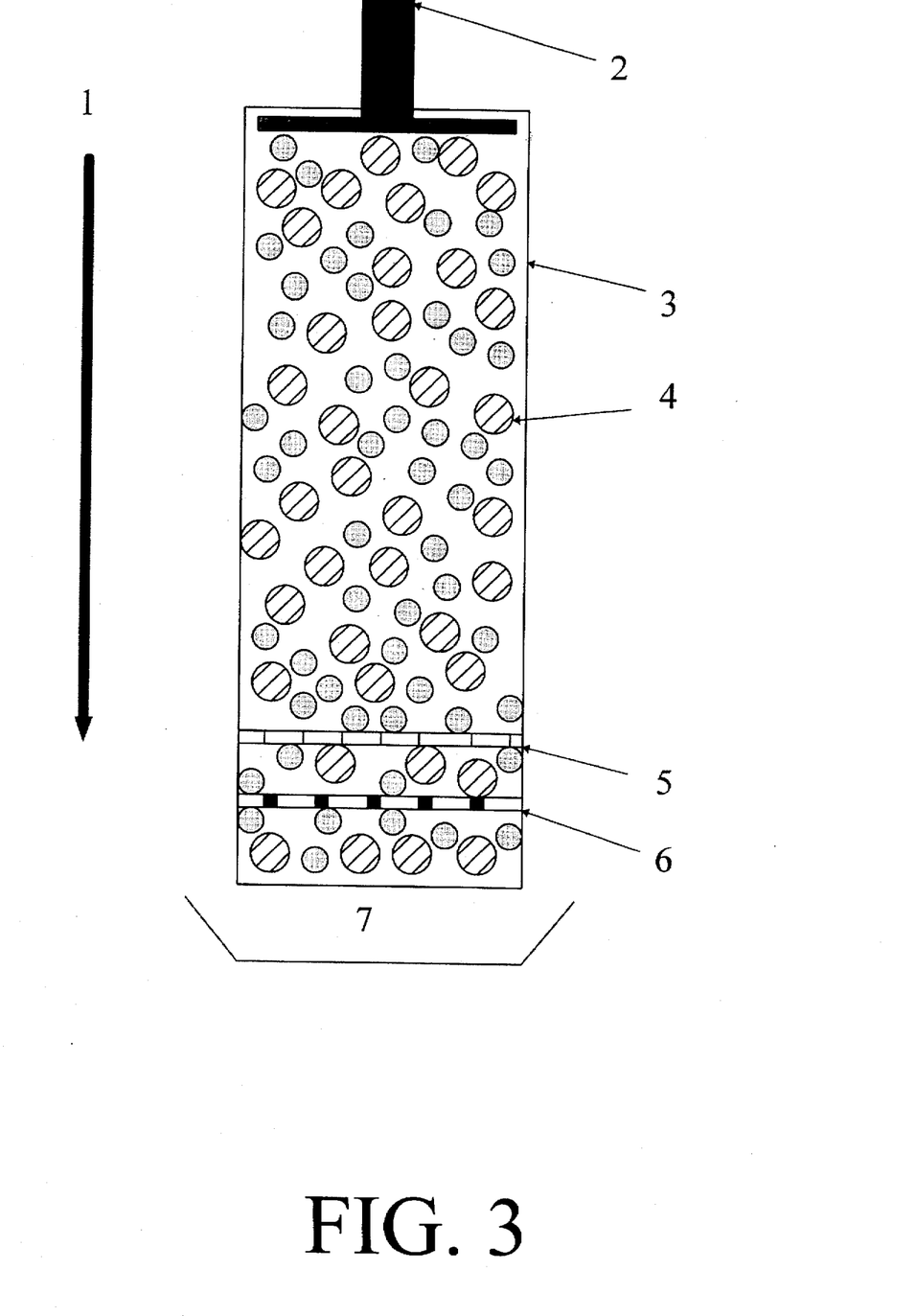
FIG. 3 is a schematic diagram of a multi-orifice impedance counter; wherein reference numeral 1 indicates the direction of flow through the column; reference numeral 2 indicates a plunger means for forcing material downward in the column; reference numerals 3 and 4 are different-sized hybridization beads; reference numeral 5 is an optional filter for extracting unwanted particles; reference numeral 6 indicates an array of orifices for measuring differential impedance; and reference numeral 7 is a collection chamber.
Figure 4:
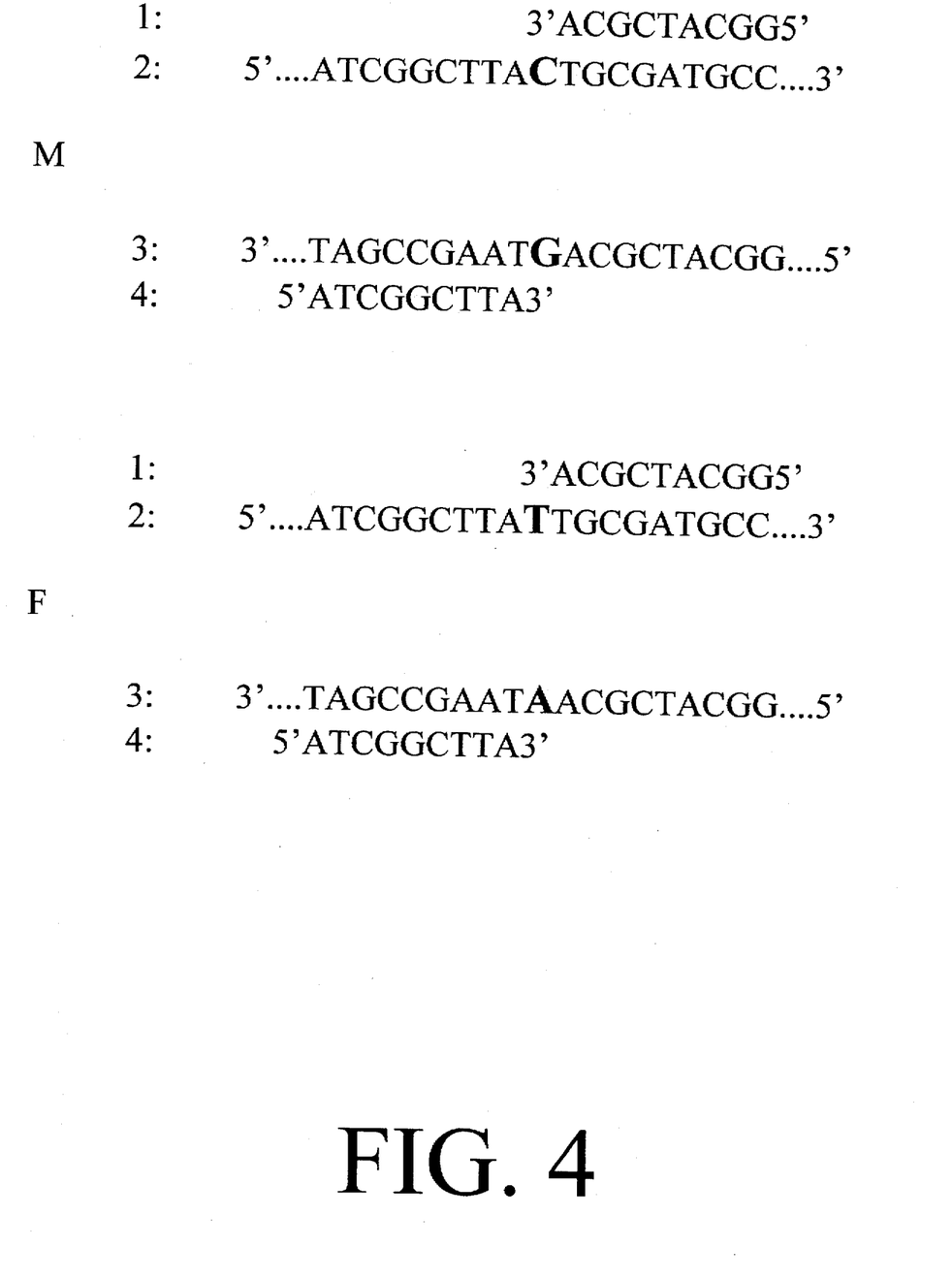
FIG. 4 is a diagram showing primers useful for the detection of single base polymorphisms.

An oligonucleotide probe is constructed that is complementary to a portion of the region of single-base polymorphism, said portion ending at the nucleotide that is immediately 3' to the polymorphic nucleotide, regardless of whether the 5'-3' (coding) strand or the 3'-5' (anticoding) strand is used as a template. FIG. 3 shows four possible probes that are immediately 3' to the polymorphic nucleotide for each of four possible template strands as described above (the Sequences in FIG. 3 are hypothetical and are not intended to represent any actual sequence). The sequence labeled M1 is SEQ ID NO:1; the sequence labeled M2 is SEQ ID NO:2; the sequence labeled M3 is SEQ ID NO:3; the sequence labeled M4 is SEQ ID NO:4; the sequence labeled F1 is SEQ ID NO:5; the sequence labeled F2 is SEQ ID NO:6; the sequence labeled F3 is SEQ ID NO:7; and the sequence labeled F4 is SEQ ID NO:8. While either strand may be used as a template for probe binding to determine heterozygosity and/or the loss thereof, the sequence of the probe that is hybridized to the template will be different depending upon the strand used. Probes may be of any length that allows efficient and specific hybridization. FIG. 3 merely illustrates four hypothetical probes that are useful for hybridization to the hypothetical sequence shown. The length of probe sequences may be determined as appropriate for each genomic region that is analyzed. A preferable length is between about 10 and about 100 nucleotides. The size of the probe will also depend upon the size of the region surrounding the single-base polymorphism (i.e., the region 5' or 3' to the next adjacent polymorphism, if any). Details concerning the construction and hybridization of oligonucleotide probes are known in the art.

Unique probes for each polymorphic region will hybridize to regions of both maternal and paternal alleles up to, but not including, the polymorphic nucleotide, which, in a heterozygote, will be different in the maternal and paternal alleles. FIG. 3 shows only a small portion of the region surrounding the polymorphic nucleotide. The alleles shown in FIG. 3 are heterozygous at the polymorphic site.

Probe is hybridized to its specific template DNA by standard methods. The sample may optionally be washed to remove unhybridized probe. To determine whether each target region bound by a probe is heterozygous or homozygous at the polymorphic nucleotide, a modification of the dideoxy chain termination method as reported in Sanger, *Proc. Nat'l Acad. Sci (USA)*, 74:5463–5467 (1977), incorporated by reference herein, is used. The method involves using at least two of the four common 2', 3'-dideoxy nucleoside triphosphates (ddATP, ddCTP, ddGTP, and ddTTP). A different detectable label is attached to each dideoxy nucleoside triphosphate (ddNTP) according to methods known in the art. Differentially-labeled ddNTPs are available commercially, for example, from Perkin Elmer Corporation (Cat. No. 401456). At least two labeled ddNTPs then are exposed to each sample having probe hybridized to maternal and paternal alleles as described above. The choice of which two ddNTPs are used will depend upon the nucleotides at the heterozygous polymorphic site. Any 3' modified nucleoside triphosphate may be used in the method as long as the 3' modification prevents binding of an additional 3' nucleotide (i.e. probe extension) and does not inhibit binding of the modified nucleotide to the 3' end of the probe. A DNA polymerase, such as Sequenase™(Perkin-Elmer), is added to the sample mixture. Using the allelic strands as primer, the polymerase will add one ddNTP to the 3' end of the probe, the incorporated ddNTP will be complementary to the nucleotide that exists at the single-base polymorphic site. Because the ddNTPs have no 3' hydroxyl, further elongation of the hybridized probe will not occur. After completion, the sample is washed to remove excess ddNTPs. Label is then counted in each sample. The presence of two differentially-labeled ddNTPs in a sample is indicative of heterozygosity at the polymorphic site.

It is not necessary to determine the amount of each label present in the sample in order to establish heterozygosity or homozygosity. For Example, differentially-labeled deoxynucleoside triphosphates may be used for a determination of heterozygosity or homozygosity. The mere fact that two different labeled dideoxy nucleotides are incorporated into the probe means that the single-base polymorphic site being analyzed is heterozygous. However, determination of sites at which a patient is polymorphic is useful in order to establish a baseline of polymorphisms which may be used in future tests to detect changes in polymorphic sites which may be indicative of cancer. The existence of polymorphisms may be determined by methods taught herein, by gel electrophoresis or by other standard methods.

In the case in which heterozygosity exists at the polymorphic site, counting the amount of each of the two differentially-labeled ddNTPs allows a determination of whether there is a loss of heterozygosity (i.e., a deletion) in a subpopulation of cells in the sample. In a normal (i.e., non-cancerous) sample containing cells that are heterozygous at the single-base polymorphic site, it is expected that the detected amount of each of the two ddNTPs added to the probe will be identical (within chosen limits of statistical significance). However, if a deletion has occurred in one of the two alleles in a subpopulation of cells in the sample, there will be a statistically-significant difference between the amounts of each of the two alleles detected via the incorporated (labeled) ddNTPs. The detection of such a difference is indicative of genomic instability within the sample. Such genomic instability indicates the possibility of cancerous or pre-cancerous cells in the sample.

In order to improve the ability to count alleles to which ddNTPs have attached accurately, ddNTPs are labeled with hybridization-type beads of different sizes as described above. Alleles with bound probe comprising a labeled ddNTP are counted as described above using a counting device, such as a Coulter counter. Also as described above, differential fluorescent labels or other counting means may be used to separately detect incorporated ddNTPs.

The detection of heterozygosity at single-base polymorphic sites and the detection of the loss of heterozygosity may be determined in separate steps. For example, probes may be hybridized immediately adjacent to but not including the nucleotide determined to be polymorphic as described above. The four ddNTPs may then be added to the sample, washed, and the presence or absence of each label may be detected. Detection of only one label indicates that the individual from whom the sample was obtained is homozygous at the site of the potential polymorphic nucleotide. Detection of two labels means that the individual is heterozygous. The heterozygous loci are recorded. As noted above, baseline determinations of heterozygosity may be done using standard methods. Once a baseline is established, future tests on that individual are performed exploiting the heterozygous loci in order to detect a loss of heterozygosity. For the detection of cancer, the heterozygous loci are typically chromosomal areas containing tumor suppressor genes, including p53, dcc, apc, and others. Using methods described herein, a "fingerprint" of heterozygous tumor suppressor loci may be constructed. Future deviation from the fingerprint (i.e., deletions) provides valuable information as to the development of cancer.

A preferred use of the foregoing methods is in the detection of colon cancer. A representative stool sample is prepared as described above. Double-stranded DNA is converted to single-stranded DNA and complement of the strand to be detected is removed from the sample. The remaining single-stranded DNA is exposed to multiple copies of a probe designed on the basis of known single-base polymorphisms in a cancer-associated allele such that the probe hybridizes with a desired number of nucleotides immediately adjacent the polymorphic nucleotides as described above. After hybridization is complete, the sample is washed and exposed to differentially-labeled ddNTPs and a DNA polymerase. The sample then is washed to remove unincorporated ddNTPs. The presence of any labeled ddNTPs is determined. If two labels are detected, the individual from whom the sample is obtained is heterozygous at the polymorphic nucleotide. The heterozygosity of the allele and the probe sequence matching the site immediately adjacent to the polymorphic allele are noted for reference in future testing for the loss of heterozygosity. Alternatively, once the patient is determined to be heterozygous at a locus, an assay may be performed immediately in the manner described above in order to determine an existing loss of heterozygosity in a subpopulation of cells in the sample.

C. Analysis of Microsatellite Instability

Microsatellites are di- or trinucleotide repeats found throughout the genome. A particular array of microsatellite repeats is often associated with a particular genomic sequence and is stably inherited under normal conditions. Expansions of microsatellite copy number typically, called "microsatellite instability," are associated with defects in mismatch repair. Accordingly, changes in a microsatellite region indicate that the patient is at risk for a mutation in other genomic regions.

In order to detect microsatellite instability as an indicator of a mutation in a cancer-associated gene, one must first identify a microsatellite region associated with the gene of interest. Such regions are typically identified on a database, such as GenBank, EMBL, and others. Once a wild-type microsatellite region associated with, for example, the p53 tumor suppressor gene, is identified, an oligonucleotide probe is constructed that spans the microsatellite region and the regions immediately 5' and immediately 3' to the microsatellite region. The precise length of probes may be determined by the experimenter. Probes are constructed that hybridize to the microsatellite region, including portions extending 5' and 3', on both the maternal and paternal alleles with which the microsatellite is associated (e.g., p53).

An appropriate sample of body tissue or fluid is obtained and processed as described herein. Double stranded DNA is denatured and an excess of maternal and paternal probes, as described above, are introduced into the sample under hybridization conditions. The probes are detectably labeled as described above. Complement of the strands to be detected may optionally be removed by methods described above. The sample is then washed to remove unhybridized probe and the amount of hybridized probe in quantitatively detected.

Quantitative detection may be accomplished by any means described herein. For example, probes may be attached to hybridization beads such that probes that bind to maternal allele are attached to beads of one size and probes that bind to paternal allele are attached to beads of a second size that is distinguishable from beads of the first size. Beads with attached probe may be counted as described above.

The detection of a statistically-significant difference between the amount of probe binding to the maternal allele and the amount of probe binding to the paternal allele is indicative of microsatellite instability. As previously mentioned, microsatellite instability can be indicative of a mutation at the locus in which the microsatellite resides. If the microsatellite region is associated with a tumor suppressor gene or an oncogene, the detection of microsatellite instability in an allele in a subpopulation of cells in a biological sample is indicative of the potential for cancer or that cancer or precancer may have already developed. Further testing as described herein (either by invasive or non-invasive means) may then be conducted.

In an alternative embodiment, a "fingerprint" of microsatellites is taken from regions associated with cancer-causing genes in a sample obtained from a patient. Such a fingerprint may be obtained by standard methods. The fingerprint comprises the sequence of wild-type microsatellites associated with the cancer-causing gene or genes. Once obtained, the fingerprint is stored and is used in future tests of samples from the same patient in order to monitor changes in microsatellite regions (i.e. microsatellite instability) that may be associated with the development of cancer. Changes in microsatellite length and/or sequence over time may be used to prescribe additional testing and/or treatment in order to detect and remove cancerous tissue at an early stage in its etiology.

Additional embodiments of the invention are apparent upon consideration of the following claims.

---

What is claimed is:

1. A method of screening for indicia of colorectal cancer in a stool sample that comprises cells and cellular debris sloughed from the circumference of the colonic epithelium, the method comprising the steps of:

(a) obtaining a sample comprising a cross-sectional portion of a stool voided by a patient; and (b) performing an assay to detect the presence of cells or cellular debris shed from a cancerous or precancerous lesion into a voided stool sample.

2. The method of claim 1, wherein said assay detects debris from a clonal population of transformed cells comprising said lesion.

3. The method of claim 2, wherein said assay detects a protein expressed by the transformed cells indicative of the presence of said cells.

4. The method of claim 2, wherein said assay detects DNA indicative of the presence of said cells.

5. The method of claim 1, further comprising the step of homogenizing said cross-sectional portion in a physiologically compatible buffer prior to step (b).

6. The method of claim 5, wherein said physiologically compatible buffer comprises a detergent and a proteinase.

7. The method of claim 1, wherein said assay detects the presence of carcinoembryonic antigen shed from said lesion.

8. The method of claim 1, wherein said assay comprises the step of exposing said sample to an antibody which specifically binds a protein in said debris.

9. The method of claim 4, wherein said DNA comprises a mutation.

10. The method of claim 9, wherein said mutation is selected from the group consisting of loss of heterozygosity and microsatellite instability.

11. The method of claim 9, wherein said mutation comprises a deletion in a tumor suppressor allele.

12. The method of claim 4, wherein said mutation comprises a loss of heterozygosity encompassing a polymorphic locus.

13. The method of claim 1, wherein said sample is an entire stool voided by a patient.

14. A method of screening for the indicia of colorectal cancer in stool containing cells and cellular debris sloughed from the circumference of the colonic epithelium, comprising:

performing an assay to detect, in a sample obtained from a cross-sectional portion of a stool, cells or cellular debris shed from a cancerous or precancerous lesion into a voided stool.

* * * * *

UNITED STATES PATENT AND TRADEMARK OFFICE
CERTIFICATE OF CORRRECTION

PATENT NO. : 5,741,650
DATED : April 21, 1998
INVENTOR(S) : Stanley N. Lapidus, et al.

It is certified that error appears in the above-identified patent and that said Letters Patent is hereby corrected as shown below:

Title page, item [56] insert the following:

FOREIGN PATENT DOCUMENTS

| | | DOCUMENT NUMBER | | | | | | PUBLICATION DATE | COUNTRY OR PATENT OFFICE | CLASS | SUBCLASS | TRANSLATION YES | NO |
|---|---|---|---|---|---|---|---|---|---|---|---|---|---|
| | | WO | 91/ | 0 | 9 | 9 | 6 | 4 | 07/11/91 | PCT | | | | |
| | | WO | 92/ | 1 | 4 | 1 | 5 | 7 | 08/20/92 | PCT | | | | |
| | | JP | 04 | 20 | 39 | 6 | 6 | A | 07/24/92 | Japan | | | | |
| | | | | | | | | | | | | | | |

Signed and Sealed this

Sixth Day of April, 1999

Attest:

Q. TODD DICKINSON

*Attesting Officer*   *Acting Commissioner of Patents and Trademarks*

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear     ( i x ) FEATURE:
        ( A ) NAME/KEY: misc_feature
        ( B ) LOCATION: 1..9
        ( D ) OTHER INFORMATION: /note= "M1"

( x i ) SEQUENCE DESCRIPTION: SEQ ID NO:1:

GGCATCGCA                9

( 2 ) INFORMATION FOR SEQ ID NO:2:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear     ( i x ) FEATURE:
        ( A ) NAME/KEY: misc_feature
        ( B ) LOCATION: 1..19
        ( D ) OTHER INFORMATION: /note= "M2"

( x i ) SEQUENCE DESCRIPTION: SEQ ID NO:2:

ATCGGCTTAC TGCGATGCC        19

( 2 ) INFORMATION FOR SEQ ID NO:3:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear     ( i x ) FEATURE:
        ( A ) NAME/KEY: misc_feature
        ( B ) LOCATION: 1..19
        ( D ) OTHER INFORMATION: /note= "M3"

( x i ) SEQUENCE DESCRIPTION: SEQ ID NO:3:

GGCATCGCAG TAAGCCGAT        19

( 2 ) INFORMATION FOR SEQ ID NO:4:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear     ( i x ) FEATURE:
        ( A ) NAME/KEY: misc_feature
        ( B ) LOCATION: 1..9

( D ) OTHER INFORMATION: /note= "M4"

( x i ) SEQUENCE DESCRIPTION: SEQ ID NO:4:

ATCGGCTTA                                                                                          9

( 2 ) INFORMATION FOR SEQ ID NO:5:

( i ) SEQUENCE CHARACTERISTICS:
      ( A ) LENGTH: 9 base pairs
      ( B ) TYPE: nucleic acid
      ( C ) STRANDEDNESS: single
      ( D ) TOPOLOGY: linear    ( i x ) FEATURE:
      ( A ) NAME/KEY: misc_feature
      ( B ) LOCATION: 1..9
      ( D ) OTHER INFORMATION: /note= "F1"

( x i ) SEQUENCE DESCRIPTION: SEQ ID NO:5:

GGCATCGCA                                                                                          9

( 2 ) INFORMATION FOR SEQ ID NO:6:

( i ) SEQUENCE CHARACTERISTICS:
      ( A ) LENGTH: 19 base pairs
      ( B ) TYPE: nucleic acid
      ( C ) STRANDEDNESS: single
      ( D ) TOPOLOGY: linear    ( i x ) FEATURE:
      ( A ) NAME/KEY: misc_feature
      ( B ) LOCATION: 1..19
      ( D ) OTHER INFORMATION: /note= "F2"

( x i ) SEQUENCE DESCRIPTION: SEQ ID NO:6:

ATCGGCTTAT TGCGATGCC                                                                              19

( 2 ) INFORMATION FOR SEQ ID NO:7:

( i ) SEQUENCE CHARACTERISTICS:
      ( A ) LENGTH: 19 base pairs
      ( B ) TYPE: nucleic acid
      ( C ) STRANDEDNESS: single
      ( D ) TOPOLOGY: linear    ( i x ) FEATURE:
      ( A ) NAME/KEY: misc_feature
      ( B ) LOCATION: 1..19
      ( D ) OTHER INFORMATION: /note= "F3"

( x i ) SEQUENCE DESCRIPTION: SEQ ID NO:7:

GGCATCGCAA TAAGCCGAT                                                                              19

( 2 ) INFORMATION FOR SEQ ID NO:8:

( i ) SEQUENCE CHARACTERISTICS:
      ( A ) LENGTH: 9 base pairs
      ( B ) TYPE: nucleic acid
      ( C ) STRANDEDNESS: single
      ( D ) TOPOLOGY: linear    ( i x ) FEATURE:
      ( A ) NAME/KEY: misc_feature
      ( B ) LOCATION: 1..9
      ( D ) OTHER INFORMATION: /note= "F4"

( x i ) SEQUENCE DESCRIPTION: SEQ ID NO:8:

ATCGGCTTA                                                                                          9